(12) United States Patent
Ogawa et al.

(10) Patent No.: US 6,310,210 B1
(45) Date of Patent: Oct. 30, 2001

(54) CAMPTOTHECIN DERIVATIVES

(75) Inventors: Takanori Ogawa; Takashi Yaegashi; Seigo Sawada; Tomio Furuta, all of Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/530,828

(22) PCT Filed: Nov. 6, 1998

(86) PCT No.: PCT/JP98/05000

§ 371 Date: May 3, 2000

§ 102(e) Date: May 3, 2000

(87) PCT Pub. No.: WO99/24430

PCT Pub. Date: May 20, 1999

(30) Foreign Application Priority Data

Nov. 6, 1997 (JP) .................................................. 9-319182

(51) Int. Cl.⁷ ................................................ C07D 471/04
(52) U.S. Cl. ........................................................... 546/70
(58) Field of Search ................................................ 546/70

(56) References Cited

U.S. PATENT DOCUMENTS

| | | |
|---|---|---|
| 4,473,692 | 9/1984 | Miyasaka et al. . |
| 4,545,880 | 10/1985 | Miyasaka et al. . |
| 4,914,205 | 4/1990 | Sawada et al. . |
| 4,939,255 | 7/1990 | Tagawa et al. . |
| 4,981,968 | 1/1991 | Wall et al. . |
| 5,049,668 | 9/1991 | Wall et al. . |
| 5,061,795 | 10/1991 | Tagawa et al. . |
| 5,061,800 | 10/1991 | Yaegashi et al. . |
| 5,122,606 | 6/1992 | Wani et al. . |
| 5,843,954 | 12/1998 | Yaegashi et al. . |

FOREIGN PATENT DOCUMENTS

| | | |
|---|---|---|
| 688547 | 8/1998 | (AU) . |
| 58-39684 | 3/1983 | (JP) . |
| 58-134095 | 8/1983 | (JP) . |
| 59-51287 | 3/1984 | (JP) . |
| 59-51289 | 3/1984 | (JP) . |
| 1-131179 | 5/1989 | (JP) . |
| 1-186892 | 7/1989 | (JP) . |
| H1-279891 | 11/1989 | (JP) . |
| H4-503505 | 6/1992 | (JP) . |
| H5-502017 | 4/1993 | (JP) . |
| H8-73461 | 3/1996 | (JP) . |
| WO 91/04260 | 4/1991 | (WO) . |
| WO 92/11263 | 7/1992 | (WO) . |

OTHER PUBLICATIONS

Design of prodrugs 1985 Elsvier pp. 4–7, 1985.*
Chemical Abstract US 5843954, USPATFUL 1998: 150956, RN # 176642–38–9, Dec. 1, 1998.*

* cited by examiner

*Primary Examiner*—Alan L. Rotman
*Assistant Examiner*—Rita Desai
(74) *Attorney, Agent, or Firm*—Wolf, Greenfield & Sacks P.C.

(57) ABSTRACT

The present invention relates to new camptothecin derivatives shown by the below formula, which are water-soluble and excellent in an anti-tumor activity, and to salts thereof.

(1)

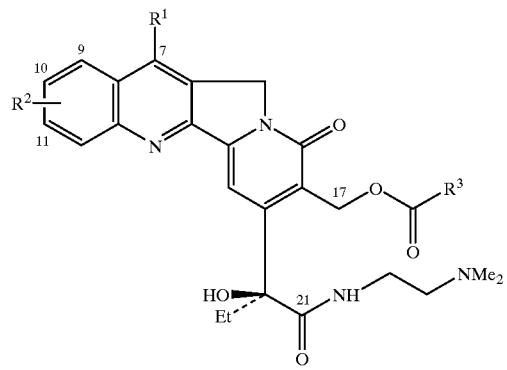

In the formula, $R^1$ represents a hydrogen atom or an alkyl group with 1–6 carbon atoms, $R^2$ represents identically or differently 0–4 alkyl groups with 1–6 carbon atoms, a halogen atom, an alkoxyl or hydroxyl group, $R^3$ represents a lower alkylamino, di-lower alkylamino, arylamino, cyclicamino or lower alkoxyl group, and salts thereof.

1 Claim, No Drawings

CAMPTOTHECIN DERIVATIVES

The present invention relates to new camptothecin derivatives which are water-soluble and excellent in an anti-tumor activity.

BACKGROUND ART

The present inventors have made an exploratory research on new camptothecin (hereinafter referred to CPT) derivatives with excellent anti-tumor activities and already provided many CPT derivatives, and it has been found out that in particular a group of derivatives prepared by a totally synthetic method have an excellent activity, which have a lower alkyl group in 7-position on the B-ring and various hetero substituents and an alkyl group in 9-, 10- and 11-position on the A-ring (see JP, A, H1-186892, U.S. Pat. No. 5,061,800). The present inventors have also made a development research for a method to make them water-soluble by various means in order to solve an administration problem, and found that regarding especially 7-ethyl CPT, the derivatives, in which the part of E-lactone ring is opened by use of the diamine and the hydroxymethyl group is protected by the appropriate acyl group, are excellent in the water solubility without decrease of an anti-tumor activity, contrasting to the E-ring opened water-soluble CPT derivatives known previously (see JP, A, H1-131179, U.S. Pat. No. 4,914,205).

Further, a new group of derivatives which were water-soluble and excellent in an anti-tumor activity were prepared and provided by derivatizing a group of derivatives having a lower alkyl group in 7-position on the B-ring and various hetero substituents and an alkyl group in 9-, 10- and 11-position on the A-ring into derivatives in which the E-lactone ring part is opened by the diamine and further the hydroxymethyl group is protected by an appropriate acyl group (see JP, A, H8-73461, AU, Pat. No. 688547). However, though these derivatives solve the water solubility problem, they are unstable in a basic water solution and not necessarily suitable for making a preparation such as an oral administration agent.

While realizing the water solubility favorable for administration, the creation of a new CPT derivative is needed which is excellent in an anti-tumor activity and in the stability in a basic water solution.

DISCLOSURE OF THE INVENTION

With the object to obtain derivatives having an extremely excellent characteristics in an anti-tumor activity, the present inventors have developed a group of new CPT derivatives in which the water solubility problem is solved and the stability in a basic water solution is improved by derivatizing a group of derivatives having a lower alkyl group in 7-position on the B-ring and various hetero substituents and an alkyl group in 9-, 10- and 11-position on the A-ring into the derivatives in which the E-lactone ring part is opened by the diamine and further the hydroxymethyl group is protected by a carbamate type or carbonate type protecting group.

The present invention provides camptothecin derivatives of the general formula (1)

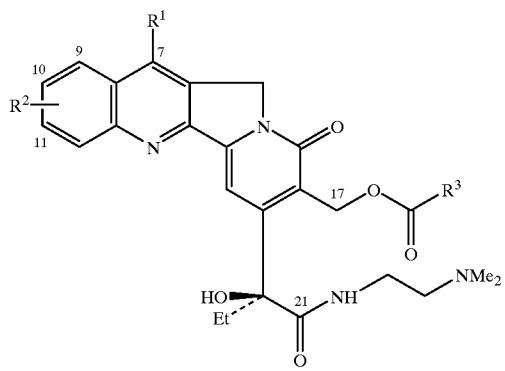

(1)

wherein $R^1$ represents a hydrogen atom or an alkyl group with 1–6 carbon atoms,
$R^2$ represents identically or differently 0–4 alkyl groups with 1–6 carbon atoms, a halogen atom, an alkoxyl or hydroxyl group,
$R^3$ represents a lower alkylamino, di-lower alkylamino, arylamino, cyclic-amino or lower alkoxyl group, and salts thereof.

In the following, the present invention is described in more detail.

BEST MODE FOR CARRYING OUT THE INVENTION

New CPT derivatives according to the present invention can be prepared using as a starting material a derivative having a hydrogen atom or a lower alkyl group in 7-position and various hetero substituents and an alkyl group in 9–12 positions, treating this with N,N-dimethylethylenediamine and subsequently acylating the 17-hydroxyl group with an appropriate acylating agent into a carbonate or carbamate type. Each group of derivatives to be a starting material are the known CPT derivatives of natural origin (9-methoxy-CPT, 10-hydroxy-CPT, 10-methoxy-CPT, 11-hydroxy-CPT, 11-methoxy-CPT, etc.) or those obtained by a known semi-synthetic or totally synthetic method (see the specification in JP, A, 58-39684, JP, A, 58-134095, U.S. Pat. No. 4,473,692, U.S. Pat. No. 4,545,880, JP, A, 59-51287, JP, A, 59-51289, JP, A, H1-279891, U.S. Pat. No. 4,939,255, U.S. Pat. No. 5,061,795, JP, A, H1-186892, U.S. Pat. No. 5,061,800, JP, A, H4-503505, U.S. Pat. No. 4,981,968, JP, A, H5-502017, U.S. Pat. No. 5,049,668, WO91/04260, WO92/11263, U.S. Pat. No. 5,122,606, etc.).

Specifically, as $R^1$ in the general formula can be selected a hydrogen atom of the natural type, or a lower alkyl group with 1–6 carbon atoms and in these methyl, ethyl or propyl group are particularly preferable.

As $R^2$ in the general formula can also be selected 0–4 substiuents on the A-ring (9- to 12-position), though specifically, in 9-, 10-, 11- or 12-positions can be selected those substituted independently or together by hydroxyl, a lower alkoxyl group such as methoxyl, a halogen such as fluorine, chlorine or bromine, or a lower alkyl group such as methyl or ethyl, wherein one having fluoro group in 11-position and one having methyl group in 10-position are preferable, in particular one having fluoro group in 11-position and methyl group in 10-position together is preferable.

Further, as $R^3$ in the general formula can be selected a lower alkylamino group such as methylamino, ethylamino, propylamino or cyclohexylamino group, a lower dialkylamino group such as dimethylamino or diethylamino group, an arylamino group such as phenylamino or fluorophenylamino group, a cyclic-amino group such as 4-isopropylaminocarbonylpiperazinyl group, or a lower alkoxyl group such as methoxyl, ethoxyl or propoxyl group. Among these phenylamino, dimethylamino and methoxyl groups are particularly preferable.

The treatment with N,N-dimethylethylenediamine and the condition of the subsequent acylation of the 17-hydroxyl group by an acylating agent can be carried out in the same method disclosed by the present inventors in JP, A, H1-131179.

Namely, in the ring opening reaction of the E-lactone ring by N,N-dimethylethylenediamine, the reaction is carried out by not using a reaction solvent but by using only an excess amount of N,N-dimethylethylenediamine letting the conversion into a E-ring opening intermediate. Subsequently, an aimed substance can be obtained in a high yield by acylating the 17-hydroxyl group with a desirable acylating agent.

The acylating agents which can be used in the above acylation reaction are not specified, though illustrative of these are the corresponding alkylisocyanates, arylisocyanates, or the corresponding alkylcarbamoylchlorides or chloroalkyl-carbonates.

In the acylation reaction, pyridine, N,N-dimethylaminopyridine or the like may be present together in the reaction as a catalyst. Further, it is possible to improve the yield of an aimed substance by keeping the condition as anhydrous as possible in processes except the ring opening reaction, that is, the acylation process, or in the later work-up processes such as a pulverization, purification and crystallization processes. The new CPT derivatives according to the invention are excellent in the solubility for water as salts with an appropriate acid such as hydrochloric acid, and excellent in the stability in an basic water solution. Further, the test results for their anti-tumor effects reveal that they have an excellent property and are extremely useful as a new anti-tumor agent.

In the following, the present invention will be explained in more detail by way of examples.

EXAMPLES

Example 1

7-Ethyl-17-methylcarbamoyloxycamptothecin-21-(2-dimethylamino)ethylamide (compound 1)

To a solution of 7-ethyl-17-hydroxycamptothecin-21-(2-dimethylamino) ethylamide 1.00 g (2.16 mmol) in methylene chloride (5 ml, dried on MS4A) was added methyl isocyanate 0.11 ml (1.81 mmol, 1.2 eq.) in an atmosphere of argon under ice-cooling and stirring. After stirring for half an hour, the mixture was stirred at room temperature (25° C.) for 6 hr. The reaction solution was purified directly by medium pressure silica gel chromatography ($CHCl_3$:MeOH) to give the title compound 582 mg (52%) as a pale yellow crystal.

mp 188–190° C. (decomp)

IR (KBr) 3300, 1685, 1645, 1590, 1510, 1260 cm.$^{-1}$ $^1$H-NMR (400 MHz, $CDCl_3$) δ1.07 (t, J=7.3 Hz, 3H, 18-$CH_3$), 1.34 (t, J=7.7 Hz, 3H, 7-$CH_2CH_3$), 2.23–2.52 (m, 4H, $CH_2N(CH_3)_2$ and 19-$CH_2$), 2.26 (s, 6H, $N(CH_3)_2$), 2.76 and 2.78 (s, 3H, $NHCH_3$ two rotamors), 3.06–3.11 (m, 2H, 7-$CH_2CH_3$), 3.34–3.45 (m, 2H, $CONHCH_2$), 5.05 (d, J=18.8 Hz, 1H, 5-$CH_2$), 5.12 (d, J=18.8 Hz, 1H, 5-$CH_2$), 5.35 (d, J=12.0 Hz, 1H, 17-$OCH_2$), 5.61 (d, J=12.0 Hz, 1H, 17-$OCH_2$), 7.48–7.50 (m, 1H, 10-H), 7.59 (s, 1H, 14-H), 7.67–7.69 (m, 1H, 11-H), 7.88 (d, J=8.3 Hz, 1H, 9-H), 8.08 (d, J=8.3 Hz, 1H, 12-H)

SI-MS m/e 522 ($M^+$+1)

Example 2

7-Ethyl-17-ethylcarbamoyloxycamptothecin-21-(2-dimethylamino)ethylamide (compound 2)

Except using ethyl isocyanate, the reaction and the after-treatment were carried out according to the method described in the example 1 to give the title compound 212 mg (18%) as a pale yellow crystal.

mp 168–170° C. (decomp)

IR (KBr) 3305, 1685, 1650, 1595, 1510, 1255 cm$^{-1}$ $^1$H-NMR (400 MHz, $CDCl_3$) δ8.06 (t, J=7.2 Hz, 3H, 18-$CH_3$), 1.12 (t, J=7.2 Hz, 3H, $NHCH_2CH_3$), 1.34 (t, J=7.7 Hz, 3H, 7-$CH_2CH_3$), 2.25–2.54 (m, 4H, $CH_2N(CH_3)_2$ and 19-$CH_2$), 2.29 (s, 6H, $N(CH_3)_2$), 3.02–3.11 (m, 2H, 7-$CH_2CH_3$), 3.16–3.23 (m, 2H, $NHCH_2CH_3$), 3.32–3.51 (m, 2H, $CONHCH_2$), 5.01 (d, J=18.7 Hz, 1H, 5-$CH_2$), 5.08 (d, J=18.7 Hz, 1H, 5-$CH_2$), 5.34 (d, J=11.8 Hz, 1H, 17-$OCH_2$), 5.57 (d, J=11.8 Hz, 1H, 17-$OCH_2$), 7.40–7.48 (m, 1H, 10-H), 7.58 (s, 1H, 14-H), 7.61–7.69 (m, 1H, 11-H), 7.83 (d, J=8.3 Hz, 1H, 9-H), 8.03 (d, J=8.3 Hz, 1H, 12-H)

SI-MS m/e 536 ($M^+$+1)

Example 3

7-Ethyl-17-n-propylcarbamoyloxycamptothecin-21-(2-dimethylamino)ethylamide (compound 3)

Except using n-propyl isocyanate, the reaction and the after-treatment were carried out according to the method described in the example 1 to give the title compound 240 mg (20%) as a pale yellow crystal.

mp 170–171° C. (decomp)

IR (KBr) 3320, 1680, 1650, 1590, 1510, 1265 cm$^{-1}$ $^1$H-NMR (400 MHz, $CDCl_3$) δ0.89 (t, J=7.3 Hz, 3H, $CH_2CH_2CH_3$), 1.08 (t, J=7.2 Hz, 3H, 18-$CH_3$), 1.34 (t, J=7.7 Hz, 3H, 7-$CH_2CH_3$), 1.47–1.53 (m, 2H, $CH_2CH_2CH_3$), 2.25 (s, 6H, $N(CH_3)_2$), 2.25–2.50 (m, 4H, $CH_2N(CH_3)_2$ and 19-$CH_2$), 3.07–3.14 (m, 4H, 7-$CH_2CH_3$ and $NHCH_2CH_2CH_3$), 3.36–3.47 (m, 2H, $CONHCH_2$), 5.05 (d, J=18.8 Hz, 1H, 5-$CH_2$), 5.11 (d, J=18.8 Hz, 1H, 5-$CH_2$), 5.34 (d, J=12.1 Hz, 1H, 17-$OCH_2$), 5.65 (d, J=12.1 Hz, 1H, 17-$OCH_2$), 6.83 (brs, 1H, OH), 7.47–7.51 (m, 1H, 10-H), 7.56–7.61 (m, 1H, NH), 7.60 (s, 1H, 14-H), 7.67–7.70 (m, 1H, 11-H), 7.88 (d, J=8.3 Hz, 1H, 9-H), 8.08 (d, J=8.5 Hz, 1H, 12-H)

SI-MS m/e 550($M^+$+1)

Example 4

7-Ethyl-17-iso-propylcarbamoyloxycamptothecin-21-(2-dimethylamino)ethylamide (compound 4)

Except using iso-propyl isocyanate, the reaction and the after-treatment were carried out according to the method described in the example 1 to give the title compound 938 mg (79%) as a pale yellow crystal.

mp 179–180° C. (decomp)

IR (KBr) 3300, 1685, 1650, 1595, 1510, 1250 cm$^{-1}$ $^1$H-NMR (400 MHz, $CDCl_3$) δ1.06 (t, J=7.2 Hz, 3H, 18-$CH_3$), 1.11 (d, J=6.6 Hz, 3H, $CH(CH_3)_2$), 1.14 (d, J=6.6

Hz, 3H, CH(CH$_3$)$_2$), 1.36 (t, J=7.6 Hz, 3H, 7-CH$_2$CH$_3$), 2.29 (s, 6H, N(CH$_3$)$_2$), 2.31–2.51 (m, 4H, CH$_2$N(CH$_3$)$_2$ and 19-CH$_2$), 3.09–3.15 (m, 2H, 7-CH$_2$CH$_3$), 3.34–3.48 (m, 2H, CONHCH$_2$), 3.73–3.82 (m, 1H, CH(CH$_3$)$_2$), 5.09 (d, J=18.8 Hz, 1H, 5-CH$_2$), 5.16 (d, J=18.8 Hz, 1H, 5-CH$_2$), 5.31 (d, J=11.6 Hz, 1H, 17-OCH$_2$), 5.69 (d, J=11.6 Hz, 1H, 17-OCH$_2$), 7.53–7.57 (m, 2H, 10-H and NH), 7.63 (s, 1H, 14-H), 7.69–7.73 (m, 1H, 11-H), 7.94–7.96 (m, 1H, 9-H), 8.11–8.13 (m, 1H, 12-H)

SI-MS m/e 550(M$^+$+1)

Example 5

17-n-Butylcarbamoyloxy-7-ethylcamptothecin-21-(2-dimethylamino)ethylamide (compound 5)

Except using n-butyl isocyanate, the reaction and the after-treatment were carried out according to the method described in the example 1 to give the title compound 598 mg (49%) as a pale yellow crystal.

mp 170–172° C. (decomp)

IR (KBr) 3300, 1680, 1650, 1590, 1510, 1460, 1250 cm$^{-1}$ $^1$H-NMR (400 MHz, CDCl$_3$) δ0.89 (t, J=7.3 Hz, 3H, NCH$_2$CH$_2$CH$_2$CH$_3$), 1.05 (t, J=7.2 Hz, 3H, 18-CH$_3$), 1.26–1.49 (m, 4H, CH$_2$CH$_2$CH$_2$CH$_3$), 1.36 (t, J=7.7 Hz, 3H, 7-CH$_2$CH$_3$), 2.28–2.53 (m, 4H, CH$_2$N(CH$_3$)$_2$ and 19-CH$_2$), 2.31 (s, 6H, N(CH$_3$)$_2$), 3.10–3.17 (m, 4H, 7-CH$_2$CH$_3$ and NHCH$_2$CH$_2$CH$_2$CH$_3$), 3.35–3.46 (m, 2H, CONHCH$_2$), 5.11 (d, J=18.5 Hz, 2H, 5-CH$_2$), 5.14 (d, J=18.5 Hz, 2H, 5-CH$_2$), 5.23 (brs, 1H, NH), 5.33 (d, J=12.1 Hz, 1H, 17-OCH$_2$), 5.69 (d, J=12.1 Hz, 1H, 17-OCH$_2$), 6.46 (brs, 1H, OH), 7.55–7.59 (m, 2H, 10-H and NH), 7.64 (s, 1H, 14-H), 7.70–7.74 (m, 1H, 11-H), 7.97 (d, J=7.6 Hz, 1H, 9-H), 8.13 (d, J=8.3 Hz, 1H, 12-H)

SI-MS m/e 564 (M$^+$+1)

Example 6

7-Ethyl-17-c-hexylcarbamoyloxycamptothecin-21-(2-dimethylamino)ethylamide (compound 6)

Except using c-hexyl isocyanate, the reaction and the after-treatment were carried out according to the method described in the example 1 to give the title compound 888 mg (70%) as a pale yellow crystal.

mp 176–179° C. (decomp)

IR (KBr) 3290, 1650, 1595, 1510, 1450, 1230 cm$^{-1}$ $^1$H-NMR (400 MHz, CDCl$_3$) δ5 1.05–1.37 (m, 3H, CH$_2$), 1.06 (t, J=7.2 Hz, 3H, 18-CH$_3$), 1.36 (t, J=7.6 Hz, 3H, 7-CH$_2$CH$_3$), 1.52–1.72 (m, 3H, CH$_2$), 1.82–1.93 (m, 2H, CH$_2$), 2.05–2.21 (m, 2H, CH$_2$), 2.29 (s, 6H, N(CH$_3$)$_2$), 2.32–2.52 (m, 4H, CH$_2$N(CH$_3$)$_2$ and 19-CH$_2$), 3.09–3.15 (m, 2H, 7-CH$_2$CH$_3$), 3.34–3.49 (m, 3H, CONHCH$_2$ and NHCH(CH$_2$)$_2$), 5.09 (d, J=18.5 Hz, 1H, 5-CH$_2$), 5.16 (d, J=18.5 Hz, 1H, 5-CH$_2$), 5.30 (d, J=12.0 Hz, 1H, 17-OCH$_2$), 5.69 (d, J=12.0 Hz, 1H, 17-OCH$_2$), 7.52–7.60 (m, 2H, 10-H and NH), 7.64 (s, 1H, 14-H), 7.69–7.71 (m, 1H, 11-H), 7.95 (d, J=8.3 Hz, 1H, 12-H), 8.13 (d, J=8.3 Hz, 1H, 12-H)

SI-MS m/e 590(M$^+$+1)

Example 7

7-Ethyl-17-phenylcarbamoyloxycamptothecin-21-(2-dimethylamino)ethylamide (compound 7)

Except using phenyl isocyanate, the reaction and the after-treatment were carried out according to the method described in the example 1 to give the title compound 650 mg (52%) as a pale yellow crystal.

mp 140–146° C. (decomp)

IR (KBr) 3315, 1715, 1680, 1650, 1595, 1530, 1210 cm$^{-1}$ $^1$H-NMR (400 MHz, CDCl$_3$) δ1.07 (t, J=7.1 Hz, 3H, 18-CH$_3$), 1.30 (t, J=7.6 Hz, 3H, 7-CH$_2$CH$_3$), 2.13 (s, 6H, N(CH$_3$)$_2$), 2.13–2.53 (m, 4H, CH$_2$N(CH$_3$)$_2$ and 19-CH$_2$), 2.89–3.05 (m, 2H, 7-CH$_2$CH$_3$), 3.30–3.45 (m, 2H, CONHCH$_2$), 4.90 (d, J=18.7 Hz, 1H, 5-CH$_2$), 4.98 (d, J=18.7 Hz, 1H, 5-CH$_2$), 5.51 (d, J=11.5 Hz, 1H, 17-OCH$_2$), 5.54 (d, J=11.5 Hz, 1H, 17-OCH$_2$), 5.85 (brs, 1H, OH), 6.94–6.98 (m, 1H, C$_6$H$_5$-p), 7.19–7.23 (m, 2H, C$_6$H$_5$-m), 7.33–7.37 (m, 1H, 10-H), 7.42–7.44 (m, 2H, C$_6$H$_5$-o), 7.50 (s, 1H, 14-H), 7.56–7.60 (m, 1H, 11-H), 7.67 (d, J=8.4 Hz, 1H, 9-H), 7.92 (d, J=8.3 Hz, 1H, 12-H)

SI-MS m/e 584(M$^+$+1)

Example 8

7-Ethyl-17-(2-fluorophenylcarbamoyloxy)-camptothecin-21-(2-dimethylamino)ethylamide (compound 8)

Except using 2-fluorophenyl isocyanate, the reaction and the after-treatment were carried out according to the method described in the example 1 to give the title compound 793 mg (61%) as a pale yellow crystal.

mp 120–125° C. (decomp)

IR (KBr) 3385, 1715, 1650, 1595, 1520, 1220 cm$^{-1}$ $^1$H-NMR (400 MHz, CDCl$_3$) δ5 1.08 (t, J=7.2 Hz, 3H, 18-CH$_3$), 1.35 (t, J=7.7 Hz, 3H, 7-CH$_2$CH$_3$), 2.27 (s, 6H, N(CH$_3$)$_2$), 2.31–2.57 (m, 4H, CH$_2$N(CH$_3$)$_2$ and 19-CH$_2$), 3.05–3.12 (m, 2H, 7-CH$_2$CH$_3$), 3.34–3.52 (m, 2H, CONHCH$_2$), 5.08 (d, J=18.8 Hz, 1H, 5-CH$_2$), 5.15 (d, J=18.8 Hz, 1H, 5-CH$_2$), 5.56 (d, J=11.7 Hz, 1H, 17-OCH$_2$), 5.75 (d, J=11.7 Hz, 1H, 17-OCH$_2$), 6.96–7.08 (m, 3H, C$_6$H$_4$—F), 7.31 (brs, 1H, NH), 7.50–7.54 (m, 2H, 10-H and C$_6$H$_4$—F), 7.62 (s, 1H, 14-H), 7.68–7.73 (m, 1H, 11-H), 7.90 (d, J=8.8 Hz, 1H, 9-H), 8.06–8.10 (m, 2H, 12-H and NH)

SI-MS m/e 602(M$^+$+1)

Example 9

7-Ethyl-17-(3-fluorophenylcarbamoyloxy)-camptothecin-21-(2-dimethylamino)ethylamide (compound 9)

Except using 3-fluorophenyl isocyanate, the reaction and the after-treatment were carried out according to the method described in the example 1 to give the title compound 1.20 g (92%) as a pale yellow crystal.

mp 143–147° (decomp)

IR (KBr) 3275, 1715, 1648, 1594, 1542, 1218 cm$^{-1}$ $^1$H-NMR (400 MHz, CDCl$_3$) δ6 1.06 (t, J=7.2 Hz, 3H, 18-CH$_3$), 1.28 (t, J=7.6 Hz, 3H, 7-CH$_2$CH$_3$), 2.11–2.54 (m, 4H, CH$_2$N(CH$_3$)$_2$ and 19-CH$_2$), 2.14 (s, 6H, N(CH$_3$)$_2$), 2.85–2.98 (m, 2H, 7-CH$_2$CH$_3$), 3.23–3.28 (m, 1H, CONHCH$_2$), 3.39–3.44 (m, 1H, CONHCH$_2$), 4.82 (d, J=18.8 Hz, 1H, 5-CH$_2$), 4.90 (d, J=18.8 Hz, 1H, 5-CH$_2$), 5.43 (s, 2H, 17-OCH$_2$), 6.47–6.49 (m, 1H, NH), 6.99–7.06 (m, 2H, C$_6$H$_4$—F), 7.28–7.32 (m, 2H, C$_6$H$_4$—F and 10-H), 7.45 (s, 1H, 14-H), 7.52–7.64 (m, 3H, 11-H and 9-H and C$_6$H$_4$—F), 7.85 (d, J=8.3 Hz, 1H, 12-H), 8.32 (brs, 1H, NH)

SI-MS m/e 602(M$^+$+1)

Example 10

7-Ethyl-17-(4-fluorophenylcarbamoyloxy)-camptothecin-21-(2-dimethylamino)ethylamide (compound 10)

Except using 4-fluorophenyl isocyanate, the reaction and the after-treatment were carried out according to the method described in the example 1 to give the title compound 1.20 g (93%) as a pale yellow crystal.

mp 138–143° C. (decomp)

IR (KBr) 3275, 1715, 1650, 1595, 1540, 1220 cm$^{-1}$ $^1$H-NMR (400 MHz, CDCl$_3$) δ6 1.06 (t, J=7.2 Hz, 3H, 18-CH$_3$), 1.32 (t, J=7.7 Hz, 3H, 7-CH$_2$CH$_3$), 2.17 (s, 6H, N(CH$_3$)$_2$), 2.24–2.52 (m, 4H, CH$_2$N(CH$_3$)$_2$ and 19-CH$_2$), 2.99–3.05 (m, 2H, 7-CH$_2$CH$_3$), 3.29–3.45 (m, 2H, CONHCH$_2$), 4.94 (d, J=18.5 Hz, 1H, 5-CH$_2$), 5.02 (d, J=18.5 Hz, 1H, 5-CH$_2$), 5.46 (d, J=11.6 Hz, lH, 17-OCH$_2$), 5.54 (d, J=11.6 Hz, 1H, 17-OCH$_2$), 6.87–6.91 (m, 2H, C$_6$H$_4$-m-F), 7.33–7.37 (m, 2H, C$_6$H4-o-F), 7.38–7.42 (m, 1H, 10-H) , 7.50 (s, 1H, 14-H), 7.59–7.62 (m, 2H, 11-H and NH), 7.74 (d, J=8.3 Hz, 1H, 9-H), 7.83 (brs, 1H, NH), 7.94 (d, J=8.5 Hz, 1H, 12-H)

SI-MS m/e 602(M$^+$+1)

Example 11

7-Ethyl-17-(1-naphthylcarbamoyloxy)-camptothecin-21-(2-dimethylamino)ethylamide (compound 11)

Except using 1-naphthyl isocyanate, the reaction and the after-treatment were carried out according to the method described in the example 1 to give the title compound 1.08 g (79%) as a pale yellow crystal.

mp 155–159° C. (decomp)

IR (KBr) 3350, 1690, 1650, 1595, 1520, 1455, 1215 cm$^{-1}$ $^1$H-NMR (400 MHz, DMSO-d$_6$) δ0.93 (t, J=7.2 Hz, 3H, 18-CH$_3$), 1.35 (t, J=7.6 Hz, 3H, 7-CH$_2$CH$_3$), 2.09 (s, 6H, N(CH$_3$)$_2$), 2.12–2.34 (m, 4H, CH$_2$N(CH$_3$)$_2$and 19-CH$_2$), 3.16–3.29 (m, 4H, 7-CH$_2$CH$_3$and CONHCH$_2$), 5.34 (s, 2H, 5-CH$_2$), 5.43 (d, J=10.7 Hz, 1H, 17-OCH$_2$), 5.57 (d, J=10.7 Hz, 1H, 17-OCH$_2$), 6.33 (s, 1H, OH), 7.47–7.52 (m, 2H), 7.49 (s, 1H, 14-H), 7.63–7.65 (m, 1H), 7.71–7.76 (m, 2H), 7.84–7.92 (m, 3H), 8.08–8.11 (m, 1H), 8.20 (d, J=8.5 Hz, 1H, 9-H), 8.30 (d, J=9.0 Hz, 1H, 12-H)

SI-MS m/e 634 (M$^+$+1)

Example 12

7-Ethyl-10-methyl-17-phenylcarbamoyloxy-camptothecin-21-(2-dimethylamino)ethylamide (compound 12)

Except using 7-Ethyl-10-methyl-17-hydroxycamptothecin-21-(2-dimethylamino)ethylamide and phenyl isocyanate, the reaction and the after-treatment were carried out according to the method described in the example 1 to give the title compound 872 mg (70%) as a pale yellow crystal.

mp 155–157° C. (decomp)

IR (KBr) 3285, 1700, 1650, 1595, 1525, 1200 cm$^{-1}$ $^1$H-NMR (400 MHz, CDCl$_3$) δ1.05 (t, J=7.1 Hz, 3H, 18-CH$_3$), 1.30 (t, J=7.6 Hz, 3H, 7-CH$_2$CH$_3$), 2.16 (s, 6H, N(CH$_3$)$_2$), 2.20–2.54 (m, 4H, CH$_2$N(CH$_3$)$_2$ and 19-CH$_2$), 2.48 (s, 3H, 10-CH$_3$), 2.89–3.07 (m, 2H, 7-CH$_2$CH$_3$), 3.23–3.47 (m, 2H, CONHCH$_2$), 4.94 (d, J=18.7 Hz, 1H, 5-CH$_2$), 5.03 (d, J=8.7 Hz, 1H, 5-CH2), 5.49 (d, J=11.7 Hz, 1H, 17-OCH$_2$), 5.57 (d, J=11.7 Hz, 1H, 17-OCH$_2$), 5.73 (brs, 1H, OH), 6.96–7.02 (m, 1H, C$_6$H$_5$-p), 7.19–7.27 (m, 2H, C$_6$H$_5$-m), 7.38–7.56 (m, 7H, C$_6$H$_5$-o, 14-H, 11-H, 9-H, NH), 7.83 (d, J=8.8 Hz, 1H, 12-H)

SI-MS m/e 598(M$^+$+1)

Example 13

7-Ethyl-11-fluoro-17-phenylcarbamoyloxy-camptothecin-21-(2-dimethylamino)ethylamide (compound 13)

Except using 7-ethyl-11-fluoro-17-hydroxy-camptothecin-21-(2-dimethylamino)ethylamide and phenyl isocyanate, the reaction and the after-treatment were carried out according to the method described in the example 1 to give the title compound 1.22 g (98%) as a pale yellow crystal.

mp 155–157° C. (decomp)

IR (KBr) 3280, 1720, 1695, 1650, 1595, 1510, 1440, 1310, 1210 cm$^{-1}$ $^1$H-NMR (400 MHz, CDCl$_3$) δ1.08 (t, J=7.3 Hz, 3H, 18-CH$_3$), 1.36 (t, J=7.6 Hz, 3H, 7-CH$_2$CH$_3$), 2.17 (s, 6H, N(CH$_3$)$_2$), 2.24–2.55 (m, 4H, CH$_2$N(CH$_3$)$_2$ and 19-CH$_2$), 3.01–3.12 (m, 2H, 7-CH$_2$CH$_3$), 3.27–3.47 (m, 2H, CONHCH$_2$), 4.96 (d, J=18.6 Hz, 1H, 5-CH$_2$), 5.04 (d, J=18.6 Hz, 1H, 5-CH$_2$), 5.49 (d, J=11.8 Hz, 1H, 17-OCH$_2$), 5.58 (d, J=11.8 Hz, 1H, 17-OCH$_2$), 5.78 (brs, 1H, OH), 6.97–7.01 (m, 1H, C$_6$H$_5$-p), 7.17–7.25 (m, 1H, 10-H), 7.21–7.25 (m, 2H, C$_6$H$_5$-m), 7.42 (d, J=7.8 Hz, 2H, C$_6$H$_5$-o), 7.49 (s, lH, 14-H), 7.51 (dd, J=2.4, 10.0 Hz, 1H, 12-H), 7.58 (brt, J=5.2 Hz, 1H, CONH), 7.81 (dd, J=6.0, 9.4 Hz, 1H, 9-H)

SI-MS m/e 602(M$^+$+1)

Example 14

17-Dimethylcarbamoyloxy-7-ethylcamptothecin-21-(2-dimethylamino)ethylamide (compound 14)

To a solution of 7-ethyl-17-hydroxycamptothecin-21-(2-dimethylamino)ethylamide 500 mg (1.08 mmol) and pyridine 0.25 ml (3.1 mmol, 2.9 %) in methylene chloride (5 ml, dried on MS4A) was added dimethylcarbamoyl chloride 0.15 ml (1.62 mmol, 1.5 eq.) in an atmosphere of argon under ice-cooling and stirring. After stirring for half an hour, the mixture was stirred at room temperature (25° C.) for 16 hr. The reaction solution was added with a saturated aqueous sodium bicarbonate solution 2 ml and 0.1 hr later was added with chloroform 50 ml, and the organic phase was washed with water, a saturated aqueous sodium chloride solution in each 10 ml, and dried over anhydrous sodium sulfate. The solvent was removed under reduced pressure, and the resulting yellow oil 710 mg was purified by silica gel chromatography (CHCl$_3$:MeOH) to give the title compound 273 mg (47%) as a pale yellow crystal.

mp 195–200° C. (decomp)

IR (KBr) 3380 1675, 1650, 1595, 1510, 1455, 1190 cm$^{-1}$ $^1$H-NMR (400 MHz, CDCl$_3$) δ1.00 (t, J=7.3 Hz, 3H, 18-CH$_3$), 1.37 (t, J=7.7 Hz, 3H, 7-CH$_2$CH$_3$), 2.39 (q, J=7.3 Hz, 2H, 19-CH$_2$), 2.65 (s, 6H, CH$_2$N(CH$_3$)$_2$), 2.90 (s, 6H, CON(CH$_3$)$_2$), 2.92–3.01 (m, 2H, CH$_2$N(CH$_3$)$_2$), 3.15 (q, J=7.7 Hz, 2H, 7-CH$_2$CH$_3$), 3.46–3.52 (m, 1H, CONHCH$_2$), 3.73–3.78 (m, 1H, CONHCH$_2$), 5.16 (d, J=18.9 Hz, 1H, 5-CH$_2$), 5.22 (d, J=18.9 Hz, 1H, 5-CH$_2$), 5.51 (d, J=11.8 Hz, 1H, 17-OCH$_2$), 5.62 (d, J=11.8 Hz, 1H, 17-OCH$_2$), 6.67 (brs, 1H, OH), 7.60–7.63 (m, 1H, 10-H), 7.63 (s, 1H, 14-H), 7.74–7.78 (m, 1H, 11-H), 7.94–7.95 (m, 1H, NH), 8.06 (d, J=8.3 Hz, 1H, 9-H), 8.18 (d, J=8.3 Hz, 1H, 12-H)

SI-MS m/e 536(M$^+$+1)

Example 15

17-Diethylcarbamoyloxy-7-ethylcamptothecin-21-(2-dimethylamino)ethylamide (compound 15)

Except using diethylcarbamoyl chloride, the reaction and the after-treatment were carried out according to the method described in the example 14 to give the title compound 132 mg (22%) as a pale yellow crystal.

mp 117–122° C. (decomp)

IR (KBr) 3380, 1650, 1595, 1510, 1475, 1275 cm$^{-1}$ $^{1}$H-NMR (400 MHz, CDCl$_3$) δ0.97 (t, J=7.3 Hz, 3H, 18-CH$_3$), 1.11 (t, J=7.1 Hz, 6H, CON(CH$_2$CH$_3$)$_2$), 1.37 (t, J=7.7 Hz, 3H, 7-CH$_2$CH$_3$), 2.34–2.45 (m, 2H, 19-CH$_2$), 2.82 (s, 6H, CH$_2$N(CH$_3$)$_2$), 3.12–3.36 (m, 8H, CH$_2$N(CH$_3$)$_2$ and 7-CH$_2$CH$_3$ and CON(CH$_2$CH$_3$)$_2$), 3.52–3.57 (m, 1H, CONHCH$_2$), 3.80–3.91 (m, 1H, CONHCH$_2$), 5.17 (d, J=18.8 Hz, 1H, 5-CH$_2$), 5.22 (d, J=18.8 Hz, 1H, 5-CH$_2$), 5.59 (s, 2H, 17-OCH$_2$), 6.77 (brs, 1H, OH), 7.61 (s, 1H, 14-H), 7.61–7.65 (m, 1H, 10-H), 7.75–7.78 (m, 1H, 11-H), 8.06 (brs, 1H, NH), 8.07 (d, J=8.1 Hz, 1H, 9-H), 8.18 (d, J=8.1 Hz, 1H, 12-H)

SI-MS m/e 564(M$^+$+1)

Example 16

7-Ethyl-17-(4-isopropylaminocarbonylmethyl-piperazino)-carbamoyloxy-camptothecin-21-(2-dimethylamino)ethylamide (compound 16)

Except using 4-(isopropylaminocarbonylmethylpiperazino) carbamoyl chloride, the reaction and the after-treatment were carried out according to the method described in the example 14 to give the title compound 448 mg (41%) as a pale yellow crystal.

mp 122–123° C. (decomp)

IR (KBr) 3315, 1650, 1595, 1515, 1455, 1420, 1235 cm$^{-1}$ $^{1}$H-NMR (400 MHz, CDCl$_3$) δ1.03 (t, J=7.3 Hz, 3H, 18-CH$_3$), 1.15 (d, J=6.3 Hz, 6H, CH(CH$_3$)$_2$), 1.38 (t, J=7.7 Hz, 3H, 7-CH$_2$CH$_3$), 2.37–2.75 (m, 8H, CH$_2$N(CH$_3$)$_2$ and 19-CH$_2$ and CH$_2$N×2), 2.48 (s, 6H, N(CH$_3$)$_2$), 2.96 (s, 2H, NCH$_2$CO), 3.14–3.20 (m, 2H, 7-CH$_2$CH$_3$), 3.42–3.51 (m, 6H, CONHCH$_2$ and OCONCH$_2$×2), 4.05–4.11 (m, 1H, CONHCH(CH$_3$)$_2$), 5.17 (d, J=18.7 Hz, 1H, 5-CH$_2$), 5.23 (d, J=18.7 Hz, 1H, 5-CH$_2$), 5.47 (d, J=11.6Hz, 1H, 17-OCH$_2$), 5.69 (d, J=11.6 Hz, 1H, 17-OCH$_2$), 6.83 (d, J=8.1 Hz, 1H, CONHCH(CH$_3$)$_2$), 7.61–7.65 (m, 1H, 10-H), 7.65 (s, 1H, 14-H), 7.76–7.79 (m, 2H, 11-H and NH), 8.08 (d, J=8.3Hz, 1H, 9-H), 8.20 (d, J=9.0Hz, 1H, 12-H)

SI-MS m/e 676(M$^+$+1)

Example 17

17-Dimethylcarbamoyloxy-7-ethyl-11-fluoro-10-methylcamptothecin-21-(2-dimethylamino)ethylamide (compound 17)

Except using 7-ethyl-11-fluoro-17-hydroxy-10-methylcamptothecin-21-(2-dimethylamino)ethylamide and dimethylcarbamoyl chloride, the reaction and the after-treatment were carried out according to the method described in the example 14 to give the title compound 167 mg (27%) as a pale yellow crystal.

mp 208–212° (decomp)

IR (KBr) 3380, 1670, 1605, 1510, 1450, 1190 cm$^{-1}$ $^{1}$H-NMR (400 MHz, CDCl$_3$) δ0.98 (t, J=7.3 Hz, 3H, 18-CH$_3$), 1.34 (t, J=7.8 Hz, 3H, 7-CH$_2$CH$_3$), 2.28–2.42 (m, 2H, 19-CH$_2$), 2.50 (s, 3H, 10-CH$_3$), 2.56 (s, 6H, CH$_2$N(CH$_3$)$_2$), 2.78–2.98 (m, 2H, CH$_2$N(CH$_3$)$_2$), 2.87 (s, 6H, CON(CH$_3$)$_2$), 3.10 (q, J=7.8 Hz, 2H, 7-CH$_2$CH$_3$), 3.38–3.50 (m, 1H, CONHCH$_2$), 3.60–3.74 (m, 1H, CONHCH$_2$), 5.11 (d, J=18.8 Hz, 1H, 5-CH$_2$), 5.17 (d, J=18.8 Hz, 1H, 5-CH$_2$), 5.44 (d, J=11.8 Hz, 1H, 17-OCH$_2$), 5.61 (d, J=11.8 Hz, 1H, 17-OCH$_2$), 6.71 (brs, 1H, OH), 7.57 (s, 1H, 14-H), 7.71 (d, J=10.7 Hz, 1H, 12-H), 7.77–7.90 (br, 1H, NH), 7.81 (d, J=7.8 Hz, 1H, 9-H)

SI-MS m/e 568 (M$^+$+1)

Example 18

7-Ethyl-17-methoxycarbonyloxycamptothecin-21-(2-dimethylamino)ethylamide (compound 18)

To a solution of 7-ethyl-17-hydroxycamptothecin-21-(2-dimethylamino)ethylamide 200 mg (0.431 mmol) and pyridine 0.1 ml (1.24 mmol, 2.9 eq.) in methylene chloride (2 ml) was added methyl chlorocarbonate 0.04 ml (0.521 mmol, 1.2 eq.) in an atmosphere of argon under ice-cooling and stirring. After stirring for half an hour, the reaction solution was added with a saturated aqueous sodium bicarbonate solution 2 ml and stirred for 0.1 hr. The mixture was added with chloroform 20 ml, and the organic phase was washed with water, a saturated aqueous sodium chloride solution in each 10 ml, and dried over anhydrous sodium sulfate. The solvent was removed under reduced pressure, and the resulting yellow oil 250 mg was purified by silica gel chromatography (CHCl$_3$:MeOH) to give the title compound 220 mg (98%) as a pale yellow crystal.

mp 132–139° C. (decomp)

IR (KBr) 3370, 1740, 1645, 1595, 1510, 1440, 1265 cm$^{-1}$ $^{1}$H-NMR (400 MHz, CDCl$_3$) δ1.08 (t, J=7.3 Hz, 3H, 18-CH$_3$), 1.35 (t, J=7.6 Hz, 3H, 7-CH$_2$CH$_3$), 2.17–2.52 (m, 4H, CH$_2$N(CH$_3$)$_2$ and 19-CH$_2$), 2.21 (s, 6H, N(CH$_3$)$_2$), 3.05–3.16 (m, 2H, 7-CH$_2$CH$_3$), 3.34–3.46 (m, 2H, CONHCH$_2$), 3.79 (s, 3H, OCH$_3$), 5.09 (s, 2H, 5-CH$_2$), 5.61 (s, 2H, 17-OCH$_2$), 7.38–7.42 (m, 1H, NH), 7.56 (s, 1H, 14-H), 7.56–7.59 (m, 1H, 10-H), 7.72–7.76 (m, 1H, 11-H), 7.97 (d, J=8.1 Hz, 1H, 9-H), 8.12 (d, J=8.3 Hz, 1H, 12-H)

SI-MS m/e 523(M$^{30}$ +1)

Example 19

7-Ethyl-17-ethoxycarbonyloxycamptothecin-21-(2-dimethylamino)ethylamide (compound 19)

Except using ethyl chlorocarbonate, the reaction and the after-treatment were carried out according to the method described in the example 18 to give the title compound 153 mg (66%) as a pale yellow crystal.

mp 95–98° (decomp)

IR (KBr) 3365, 1740, 1645, 1595, 1505, 1455, 1255 cm$^{-1}$ $^{1}$H-NMR (400 MHz, CDCl$_3$) δ1.06 (t, J=7.3 Hz, 3H, 18-CH$_3$), 1.29 (t, J=7.1 Hz, 3H, OCH$_2$CH$_3$), 1.35 (t, J=7.7 Hz, 3H, 7-CH$_2$CH$_3$), 2.20–2.52 (m, 4H, CH$_2$N(CH$_3$)$_2$ and 19-CH$_2$), 2.25 (s, 6H, N(CH$_3$)$_2$), 3.06–3.16 (m, 2H, 7-CH$_2$CH$_3$), 3.32–3.53 (m, 2H, CONHCH$_2$), 4.21 (q, J=7.1 Hz, 2H, OCH$_2$CH$_3$), 5.09 (s, 2H, 5-CH2), 5.60 (S, 2H, 17-OCH$_2$), 7.38–7.42 (m, 1H, NH), 7.56–7.60 (m, 1H, 10-H), 7.57 (s, 1H, 14-H), 7.72–7.76 (m, 1H, 11-H), 7.98 (d, J=8.1 Hz, 1H, 9-H), 8.13 (d, J=7.8 Hz, 1H, 12-H)

SI-MS m/e 535(M$^+$−1)

Example 20

7-Ethyl-17-n-propoxycarbonyloxycamptothecin-21-(2-dimethylamino)ethylamide (compound 20)

Except using n-propyl chlorocarbonate, the reaction and the after-treatment were carried out according to the method described in the example 18 to give the title compound 241 mg (100%) as a pale yellow crystal.

mp 87–91° (decomp)

IR (KBr) 3365, 1730, 1650, 1595, 1510, 1455, 1260 cm$^{-1}$ $^1$H-NMR (400 MHz, CDCl$_3$) δ0.94 (t, J=7.3 Hz, 3H, CH$_2$CH$_2$CH$_3$), 1.07 (t, J=7.3 Hz, 3H, 18-CH$_3$), 1.35 (t, J=7.7 Hz, 3H, 7-CH$_2$CH$_3$), 1.63–1.72 (m, 2H, OCH$_2$CH$_2$CH$_3$), 2.17–2.50 (m, 4H, CH$_2$N(CH$_3$)$_2$ and 19-CH$_2$), 2.20 (s, 6H, N(CH$_3$)$_2$), 3.06–3.21 (m, 2H, 7-CH$_2$CH$_3$), 3.31–3.48 (m, 2H, CONHCH$_2$), 4.11 (t, J=6.8 Hz, 2H, OCH$_2$), 5.09 (s, 2H, 5-CH$_2$), 5.59 (s, 2H, 17-OCH$_2$), 7.33–7.36 (m, 1H, NH), 7.56 (s, 1H, 14-H), 7.56–7.60 (m, 1H, 10-H), 7.72–7.76 (m, 1H, 11-H), 7.99 (d, J=7.8 Hz, 1H, 9-H), 8.13 (d, J=7.8Hz, 1H, 12-H)

SI-MS m/e 551(M$^+$+1)

Example 21

17-n-Butoxycarbonyloxy-7-ethyl-camptothecin-21-(2l-dimethylamino)ethylamide (compound 21)

Except using n-butyl chlorocarbonate, the reaction and the after-treatment were carried out according to the method described in the example 18 to give the title compound 261 mg (100%) as a pale yellow crystal.

mp 83–86° C. (decomp)

IR (KBr) 3370, 1740, 1645, 1595, 1510, 1455, 1255 cm$^{-1}$ $^1$H-NMR (400 MHz, CDCl$_3$) δ0.91 (t, J=7.3 Hz, 3H, OCH$_2$CH$_2$CH$_2$CH$_3$), 1.06 (t, J=7.2 Hz, 3H, 18-CH$_3$), 1.36 (t, J=7.7 Hz, 3H, 7-CH$_2$CH$_3$), 1.37–1.43 (m, 2H, OCH$_2$CH$_2$CH$_2$CH$_3$), 1.59–1.67 (m, 2H, OCH$_2$CH$_2$CH$_2$CH$_3$), 2.21–2.51 (m, 4H, CH$_2$N(CH$_3$)$_2$ and 19-CH$_2$), 2.26 (s, 6H, N(CH$_3$)$_2$), 3.07–3.17 (m, 2H, 7-CH$_2$CH$_3$), 3.32–3.51 (m, 2H, CONHCH$_2$), 4.15 (t, J=6.8 Hz, 2H, OCH$_2$), 5.10 (s, 2H, 5-CH$_2$), 5.60 (s, 2H, 17-OCH$_2$), 7.35–7.39 (m, 1H, NH), 7.57 (s, 1H, 14-H), 7.57–7.61 (m, 1H, 10-H), 7.73–7.77 (m, 1H, 11-H), 7.99 (d, J=7.8 Hz, 1H, 9-H), 8.14 (d, J=7.6 Hz, 1H, 12-H)

SI-MS m/e 565(M$^+$+1)

Example 22

7-Ethyl-10-methyl-17-methoxycarbonyloxy-camptothecin-21-(2-dimethylamino)ethylamide (compound 22)

Except using 7-ethyl-17-hydroxy-10-methylcamptothecin-21-(2-dimethylamino)ethylamide and methyl chlorocarbonate, the reaction and the after-treatment were carried out according to the method described in the example 18 to give the title compound 272 mg (100%) as a pale yellow crystal.

mp 150–153° C. (decomp)

IR (KBr) 3365, 1745, 1650, 1600, 1510, 1440, 1265 cm$^{-1}$ $^1$H-NMR (400 MHz, CDCl$_3$) δ1.06 (t, J=7.32 Hz, 3H, 18-CH$_3$), 1.35 (t, J=7.7 Hz, 3H, 7-CH$_2$CH$_3$), 2.28–2.50 (m, 4H, CH$_2$N(CH$_3$)$_2$ and 19-CH$_2$), 2.25 (s, 6H, N(CH$_3$)$_2$), 2.58 (s, 3H, ArCH$_3$), 3.03–3.13 (m, 2H, 7-CH$_2$CH$_3$), 3.31–3.51 (m, 2H, CONHCH$_2$), 3.78 (s, 3H, OCH$_3$), 5.09 (s, 2H, 5-CH$_2$), 5.60 (s, 2H, 17-OCH$_2$), 7.32 (brs, 1H, NH), 7.52 (s, 1H, 14-H), 7.57 (dd, J=1.7, 8.8 Hz, 1H, 11-H), 7.72 (s, 1H, 9-H), 8.02 (d, J=8.8 Hz, 1H, 12-H)

SI-MS m/e 537(M$^+$+1)

Example 23

7-Ethyl-11-fluoro-17-methoxycarbonyloxy-camptothecin-21-(2-dimethylamino)ethylamide (compound 23)

Except using 7-ethyl-11-fluoro-17-hydroxy-10-methylcamptothecin-21-(2-dimethylamino)ethylamide and methyl chlorocarbonate, the reaction and the after-treatment were carried out according to the method described in the example 18 to give the title compound 74 mg (17%) as a pale yellow crystal. mp 150–154° C. (decomp)

IR (KBr) 3360, 1735, 1650, 1600, 1510, 1450, 1265 cm$^{-1}$ $^1$H-NMR (400 MHz, CDCl$_3$) δ1.07 (t, J=7.3 Hz, 3H, 18-CH$_3$), 1.37 (t, J=7.7 Hz, 3H, 7-CH$_2$CH$_3$), 2.17–2.32 (m, 2H, CH$_2$N(CH$_3$)$_2$), 2.41–2.48 (m, 2H, 19-CH$_2$), 2.20 (s, 6H, N(CH$_3$)$_2$), 3.10–3.20 (m, 2H, 7-CH$_2$CH$_3$), 3.30–3.48 (m, 2H, CONHCH$_2$), 3.79 (s, 3H, OCH$_3$), 5.13 (s, 2H, 5-CH$_2$), 5.58 (d, J=11.2 Hz, 1H, 17-OCH$_2$), 5.62 (d, J=11.2 Hz, 1H, 17-OCH$_2$), 7.26–7.29 (m, 1H, 10-H), 7.37–7.41 (m, 1H, NH),7.56 (s, 1H, 14-H), 7.75–7.78 (m, 1H, 12-H), 8.01–8.05 (m, 1H, 9-H)

SI-MS m/e 541(M$^+$+1)

Example 24

Preparation of hydrochloride

A corresponding camptothecin-21-(2-dimethylamino) ethylamide derivative (100–200 mg) was added with an aqueous 0.1 N HCl solution (1.05 eq.) and dissolved, if necessary, further by adding purified water. The solution was filtered using MILLEX-GV (0.22 mm Filter Unit), and the filtrate was lyophilized to give the desired hydrochloride.

The solubility of each hydrochloride prepared in purified water is shown in Table 1.

Table 1: Solubility of each hydrochloride in purified water

| Compound No. | Solubility (mg/ml) |
| --- | --- |
| Compound 1 | ≧50 |
| Compound 2 | ca. 14 |
| Compound 3 | ca. 11 |
| Compound 4 | ca. 50 |
| Compound 5 | ca. 10 |
| Compound 6 | ca. 50 |
| Compound 7 | ca. 15 |
| Compound 8 | ca. 11 |
| Compound 9 | ca. 28 |
| Compound 10 | ca. 7 |
| Compound 11 | ca. 5 |
| Compound 14 | ca. 50 |
| Compound 15 | ca. 53 |
| Compound 16 | ≧33 |
| Compound 18 | ≧50 |
| Compound 19 | ≧52 |
| Compound 20 | ≧52 |
| Compound 21 | ≧54 |

Example 25

Anti-tumor Activity

Experimental Method

5×10$^5$ cells of mouse leukemia L1210 were transplanted intraperitoneally to a group of six female CDP$_1$ mice (7 weeks old, body weight 17–19 g). A test substance was administered intraperitoneally on day 1, 5 and 9, and its life prolonging effect was observed. In a case of the administration of a test substance as an acid addition salt, it was dissolved in purified water. The total administration amount was 1.56–400 mg/kg. The anti-tumor activity was expressed by the value (T/C%) in which the ratio of the mean survival days of a drug administered group (T) to the mean survival days of a not administered group (C) is multiplied by 100. In case of a life prolongation equal to or more than 125% the drug is considered to be effective, and a therapeutic index was calculated by examining the least effective dose and the maximum tolerance dose.

Experimental Results

As for the substances obtained in the fore-mentioned examples the results of the anti-tumor activity test are shown in below Tables 2–6. As demonstrated in each Table, the new camptothecin derivatives according to the present invention show an excellent activity compared with 7-ethylcamptothecin sodium salt as a reference compound.

TABLE 2

Anti-tumor activity

| Compound No. | Total dose (mg/kg) | | | | | | |
|---|---|---|---|---|---|---|---|
| | 3.13 | 6.25 | 12.5 | 25 | 50 | 100 | 200 |
| Compound 1 | 97 | 97 | 95 | 97 | 97 | 139 | 145 |
| Compound 3 | 100 | 100 | 139 | 142 | 147 | 147 | 147 |
| Reference | 129 | 142 | 153 | 211 | 266 | 339(2/6) | 303(1/6) |

TABLE 3

Anti-tumor activity

| Compound No. | Total dose (mg/kg) | | | | | | |
|---|---|---|---|---|---|---|---|
| | 3.13 | 6.26 | 12.5 | 25 | 50 | 100 | 200 |
| Compound 5 | 88 | 98 | 120 | 137 | 151 | 168 | 176 |
| Compound 7 | 95 | 129 | 139 | 137 | 178 | 227 | 541(4/6) |
| Compound 8 | 93 | 122 | 129 | 134 | 154 | 176 | 256 |
| Compound 9 | 112 | 117 | 137 | 134 | 173 | 239 | 318 |
| Reference Compound | 134 | 139 | 141 | 200 | 222 | 410(1/6) | 244 |

TABLE 4

Anti-tumor activity

| Compound No. | Total dose (mg/kg) | | | | | | |
|---|---|---|---|---|---|---|---|
| | 3.13 | 6.25 | 12.5 | 25 | 50 | 100 | 200 |
| Compound 4 | 121 | 123 | 121 | 123 | 149 | 205 | 323(1/6) |
| Compound 10 | 115 | 118 | 123 | 136 | 174 | 221 | 310 |
| Compound 14 | 118 | 121 | 126 | 136 | 149 | 218 | 523(4/6) |
| Reference Compound | 126 | 146 | 151 | 215 | 249 | 513(4/6) | 362(1/6) |

TABLE 5

Anti-tumor activity

| Compound No. | Total dose (mg/kg) | | | | | | |
|---|---|---|---|---|---|---|---|
| | 3.13 | 6.25 | 12.5 | 25 | 50 | 100 | 200 |
| Compound 11 | 105 | 132 | 142 | 142 | 150 | 192 | 271 |
| Compound 18 | 139 | 150 | 132 | 139 | 218 | 597(5/6) | 524(4/6) |
| Reference Compound | 142 | 155 | 166 | 224 | 408(2/6) | 584(5/6) | 339(1/6) |

TABLE 6

Anti-tumor activity

| Compound No. | Total dose (mg/kg) | | | | | | |
|---|---|---|---|---|---|---|---|
| | 3.13 | 6.25 | 12.5 | 25 | 50 | 100 | 200 |
| Compound 19 | 126 | 129 | 126 | 129 | 190 | 388(2/6) | 29 |
| Compound 20 | 129 | 124 | 121 | 133 | 188 | 424(3/6) | 188 |
| Compound 21 | 124 | 126 | 131 | 129 | 138 | 195 | 157 |
| Reference Compound | 133 | 136 | 157 | 193 | 310(1/6) | 345(1/6) | 152 |

Stability test of new water-soluble camptothecin derivatives in water

1) Preparation of calibration curve:

1.05 mg of the compound 1 and 1.10 mg of the compound A (Note) were measured, dissolved in acetonitrile 10 ml to give a standard solution. 20 $\mu$l of the standard solution was tested by HPLC method (procedure condition 1). The peak area of the compound 1 and the compound A (Note), which is obtained from the chromatograph of the standard solution is measured by an automatic integration method, and the obtained area is plotted against an amount of the compound 1 and the compound A (2.1 $\mu$g and 2.2 $\mu$g) by 20 $\mu$l to prepare a calibration curve.

(Note) Compound A: 7-Ethyl-17-acetoxycamptothecin-21-(2-dimethylamino)ethylamide hydrochloride Calibration curve:

Compound 1 Y=9.29×10$^{-5}$X

Compound A Y=7.45×10$^{-5}$X

[X: peak area, Y: amounts of Compound 1 and Compound A ($\mu$g)]

[HPLC method, procedure condition 1]

Column: Inertsil ODS-3 (5-250), 40 deg.

Mobile phase: 0.01 M potassium dihydrogenphosphate-acetonitrile (3:1)

Flow rate: 1.0 ml/min

Detection: UV absorptiometer (254 nm)

2) Stability of compound 1 and compound A in each pH:

About 1 mg (×3) of the compound 1 were measured, dissolved adding a phosphate buffer 10 ml of pH 10.0, 7.0 or 5.4, stirred at room temperature (about 26° C.) to make a test solution. As to each 20 $\mu$l of the test solution at the time of dissolution, 3 hr later and 24 hr later, the tests were carried out by the HPLC method (procedure condition 1). The amounts of the compound 1 were measured from the obtained area. The amounts of the compound A in each pH were measured.

The amounts ($\mu$g/ml) of the compound 1 and the compound A at the time of dissolution, 3 hr later and 24 hr later in each pH are shown in Table 7.

TABLE 7

| Compound | | pH 10.0 | pH 7.0 | pH 5.4 |
|---|---|---|---|---|
| Compound 1 | at the time of dissolution | 109 | 105 | 118 |
| | 3 hr later | 106 | 105 | 118 |
| | 24 hr later | 97 | 105 | 118 |
| Compound A | at the time of dissolution | 102 | 110 | 126 |
| | 3 hr later | 79 | 110 | 126 |
| | 24 hr later | 16 | 107 | 124 |

3) Results:

The compound 1 was stably present at room temperature in the aqueous solutions of pH 7.0 and 5.4. Even after 24 hr there remained 89% of it in the aqueous solution of pH 10.0. Contrastingly, 84% of the compound A were hydrolyzed in the aqueous solution of pH 10.0 after 24 hr.

These results demonstrate that the 17-carbamide ester derivative is superior to the 17-ester derivative in the stability in an alkaline aqueous solution.

What is claimed is:

1. Camptothecin derivatives of the general formula (1)

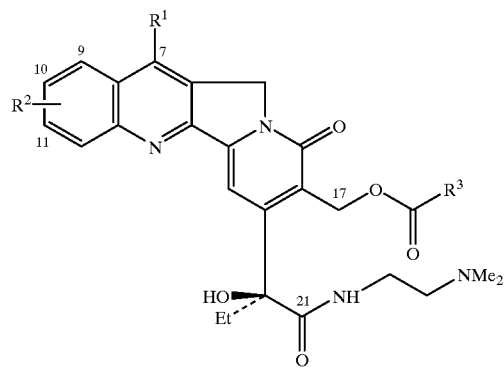

(1)

wherein $R^1$ represents a hydrogen atom or an alkyl group with 1–6 carbon atoms, $R^2$ represents identically or differently 0–4 alkyl groups with 1–6 carbon atoms, a halogen atom, an alkoxyl or hydroxyl group, $R^3$ represents a lower alkylamino, di-lower alkylamino, arylamino, cyclicamino or lower alkoxyl group, and pharmaceutically acceptable salts thereof.

* * * * *